US007022506B2

(12) United States Patent
Brighton et al.

(10) Patent No.: US 7,022,506 B2
(45) Date of Patent: Apr. 4, 2006

(54) METHOD AND DEVICE FOR TREATING OSTEOARTHRITIS, CARTILAGE DISEASE, DEFECTS AND INJURIES IN THE HUMAN KNEE

(75) Inventors: Carl T. Brighton, Malvern, PA (US); Solomon R. Pollack, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 24 days.

(21) Appl. No.: 10/457,167

(22) Filed: Jun. 9, 2003

(65) Prior Publication Data

US 2004/0006373 A1   Jan. 8, 2004

Related U.S. Application Data

(63) Continuation-in-part of application No. 10/257,126, filed as application No. PCT/US01/05991 on Feb. 23, 2001.

(60) Provisional application No. 60/184,491, filed on Feb. 23, 2000.

(51) Int. Cl.
    *C12N 13/00* (2006.01)
(52) U.S. Cl. .................... 435/173.8; 607/51
(58) Field of Classification Search ............. 435/173.8; 607/51
    See application file for complete search history.

(56) References Cited

U.S. PATENT DOCUMENTS

| 4,430,999 A | 2/1984 | Brighton et al. ............. 128/419 |
| 4,442,846 A | 4/1984 | Brighton et al. ............. 128/784 |
| 4,467,808 A | 8/1984 | Brighton et al. ......... 128/419 F |
| 4,467,809 A * | 8/1984 | Brighton ...................... 607/51 |
| 4,487,834 A | 12/1984 | Brighton ...................... 435/173 |
| 4,506,674 A | 3/1985 | Brighton et al. ............. 128/419 |
| 4,509,520 A | 4/1985 | Dugot ........................ 128/419 |
| 4,535,775 A | 8/1985 | Brighton et al. ......... 128/419 F |
| 4,549,547 A | 10/1985 | Brighton et al. ......... 128/419 F |
| 4,600,010 A | 7/1986 | Dugot ........................ 128/419 |
| 4,683,873 A | 8/1987 | Cadossi et al. ............... 128/1.5 |
| 5,014,699 A | 5/1991 | Pollack et al. .............. 128/419 |
| 5,038,797 A | 8/1991 | Batters ....................... 128/798 |
| 5,269,746 A | 12/1993 | Jacobson ..................... 600/13 |
| 5,273,033 A | 12/1993 | Hoffman ...................... 607/46 |
| 5,338,286 A | 8/1994 | Abbott et al. ................. 600/14 |
| 5,374,283 A | 12/1994 | Flick .......................... 607/46 |
| 5,743,844 A | 4/1998 | Tepper et al. ................. 600/14 |
| 5,968,527 A | 10/1999 | Litovitz ...................... 424/400 |
| 6,083,149 A | 7/2000 | Wascher et al. ............... 600/9 |
| 6,132,362 A | 10/2000 | Tepper et al. ................. 600/14 |
| 6,186,940 B1 | 2/2001 | Kirschbaum .................. 600/12 |
| 6,261,221 B1 | 7/2001 | Tepper et al. ................. 600/14 |
| 2002/0052634 A1 | 5/2002 | March ........................ 607/50 |
| 2003/0211084 A1 | 11/2003 | Brighton et al. ........... 424/93.7 |

FOREIGN PATENT DOCUMENTS

| WO | WO 00/02585 A1 | 1/2000 |
| WO | WO 01/62336 A1 | 8/2001 |
| WO | WO 2005/070136 A2 | 8/2005 |

OTHER PUBLICATIONS

Aaron, R.K., et al., "The conservative treatment of osteonecrosis of the femoral head," *Clin. Orthop.*, 1989, 249, 209-218.

Aaron, R.K., et al., "Stimulation of experimental endochondral ossification by low-energy pulsing electromagnetic fields," *J. Bone Miner. Res.*, Nov. 2, 1989, 4, 227-233.

Bassett,C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

(Continued)

*Primary Examiner*—James Ketter
(74) *Attorney, Agent, or Firm*—Woodcock Washburn, LLP

(57) ABSTRACT

A method of determining the voltage and current output required for the application of specific and selective electric and electromagnetic signals to diseased articular cartilage in the treatment of osteoarthritis, cartilage defects due to trauma or sports injury, or used as an adjunct with other therapies (cell transplantation, tissue-engineered scaffolds, growth factors, etc.) for treating cartilage defects in the human knee joint and a device for delivering such signals to a patient's knee. An analytical model of the human knee is developed whereby the total tissue volume in the human knee may be determined for comparison to the total tissue volume of the diseased tissue in the animal model using electric field and current density histograms. The voltage and current output used in the animal model is scaled based on the ratio of the total tissue volume of the diseased tissue of the human to the total tissue volume of the diseased tissue in the animal model and the resulting field is applied to the diseased tissue of the human using at least two electrodes applied to the knee or a coil or solenoid placed around the knee. The voltage of the signal applied to the electrodes, coil or solenoid is varied based on the size of the knee joint; larger knee joints require larger voltages to generate the effective electric field.

28 Claims, 15 Drawing Sheets

OTHER PUBLICATIONS

Bassett, C.A.L., et al., "Fundamental and practical aspects of therapeutic uses of pulsed electromagnetic fields (PEMSs)," *Crit. Rev. Biomed. Eng.*, 1989, 17(5), 451-529

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 62-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Goodman, R., et al., "Exposure of salivary gland cells to low-frequency electromagnetic fields alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physiochemical properties of connective tissue," *Crit. Rev. Biomed. Engng.*, 1983, 9(2), 133-198.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32.

Wang, W., et al., "The increased level of PDGF-A constributes to the increased proliferation induced by mechanical stimulation in osteoblastic cells," *Biochem. And Molecular Biol, International*, Oct. 1997, 43(2), 339-346.

Zhuang, H., et al., "Mechanical strain-induced proliferation of osteoblastic cells parallels increased TGF-$\beta$1 mRNA," *Biochem. Biophys. Res. Commun.*, 1996, 229, 449-453.

Zhuang, H., et al., "Electrical stimulation induces the level of TGF-$\beta$1 mRNA in osteoblastic cells by a mechanism involving calcium/calmodulin pathway," *Biochem. Biophys. Res. Commun.*, 1997, 237, 225-229.

Brighton, C.T., et al., "Fracture healing in the rabbit fibula when subjected to various capacitively coupled electrical fields," *J. Orthop. Res.*, 1985, 3, 331-340.

Brighton, C.T., et al., "In vitro bone-cell response to a capacitively coupled electrical field," *Clin. Orthop. Related Res.*, Dec. 1992, 285, 255-262.

Carter, E.L., et al., "Field distributions in vertebral bodies of the rat during electrical stimulation: a parametric study," *IEEE Trans. on Biomed. Eng.*, Mar. 1989, 36(3), 333-345.

Brighton, C.T., et al., "Signal transduction in electrically stimulated bone cells," *J. Bone Joint Surg. Am.*, 2001, 83-A(10), 1514-1523.

Pienkowski, D., et al., "Low-power electromagnetic stimulation of osteotomized rabbit fibuiae," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S, S163-S173.

\* cited by examiner

METHOD AND DEVICE FOR TREATING OSTEOARTHRITIS, CARTILAGE DISEASE, DEFECTS AND INJURIES IN THE HUMAN KNEE

CROSS-REFERENCE TO RELATED APPLICATIONS

The present patent application is a continuation-in-part patent application of U.S. patent application Ser. No. 10/257,126, filed Oct. 8, 2002, which is the U.S. national phase patent application of PCT/US01/05991, filed Feb. 23, 2001, which, in turn, claims the benefit of the filing date of U.S. Provisional Patent Application Ser. No. 60/184,491, filed Feb. 23, 2000.

FIELD OF THE INVENTION

The present invention is directed to the method of determining the voltage and current output required for the application of specific and selective electric and electromagnetic signals to diseased articular cartilage in the treatment of osteoarthritis, cartilage defects due to trauma or sports injuries, or as an adjunct with other therapies (e.g., cell transplantation, tissue-engineered scaffolds, growth factors, etc.) for treating cartilage defects in the human knee joint and a device for delivering such signals to a patient's knee.

BACKGROUND OF THE INVENTION

The bioelectrical interactions and activity believed to be present in a variety of biological tissues and cells are one of the least understood of the physiological processes. However, there has recently been much research into these interactions and activity regarding the growth and repair of certain tissues and cells. In particular, there has been much research into stimulation by electric and electromagnetic fields and its effect on the growth and repair of bone and cartilage. Researchers believe that such research might be useful in the development of new treatments for a variety of medical problems.

Osteoarthritis, also known as degenerative joint disease, is characterized by degeneration of articular cartilage as well as proliferation and remodeling of subchondral bone. The usual symptoms are stiffness, limitation of motion, and pain. Osteoarthritis is the most common form of arthritis, and prevalence rates increase markedly with age. It has been shown that elderly patients with self-reported osteoarthritis visit doctors twice as frequently as their unaffected peers. Such patients also experience more days of restricted activity and bed confinement compared to others in their age group. In one study, the majority of symptomatic patients became significantly disabled during an 8-year follow-up period. Massardo et al., Ann Rheum Dis 48: 893–7 (1989).

Nonsteroidal anti-inflammatory drugs (NSAIDs) remain the primary treatment modality for osteoarthritis. It is unknown whether the efficacy of NSAIDs is dependent upon their analgesic or anti-inflammatory properties or the slowing of degenerative processes in the cartilage. There is also a concern that NSAIDs may be deleterious to patients. For example, NSAIDs have well known toxic effects in the stomach, gastrointestinal tract, liver and kidney. However, aspirin inhibits proteoglycan synthesis and normal cartilaginous repair processes in animals. One study in humans suggested that indomethacin might accelerate breakdown of hip cartilage. All adverse effects appear more commonly in the elderly—the very population the most susceptible to osteoarthritis.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers that is impregnated with the mineral component of calcium phosphate (85%) and calcium carbonate (10%) that imparts rigidity to bone. While osteoporosis is generally thought as afflicting the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, which may ultimately lead to a secondary fracture in an already osteoporotic skeleton. Diminished bone density may lead to vertebrae collapse, fractures of hips, lower arms, wrists, ankles as well as incapacitating pains. Alternative nonsurgical therapies for such diseases are needed.

Pulsed electromagnetic fields (PEMF) and capacitive coupling (CC) have been used widely to treat nonhealing fractures and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. Pulsed electromagnetic fields generate small, induced currents (Faraday currents) in the highly conductive extracellular fluid, while capacitive coupling directly causes currents in the tissues; both PEMFs and CC thereby mimic endogeneous electrical currents.

The endogeneous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials apparently serve a purpose in cartilage similar to that in bone, and, along with mechanical strain, lead to signal transduction that is capable of stimulating chondrocyte synthesis of matrix components.

The main application of direct current, capacitive coupling, and PEMFs has been in orthopedics in healing of nonunion bone fractures (Brighton et al., *J. Bone Joint Surg.,* 63: 2–13, 1981; Brighton and Pollack, *J. Bone Joint Surg.,* 67: 577–585, 1985; Bassett et al., *Crit. Rev. Biomed. Eng.,* 17: 451–529, 1989; Bassett et al., *JAMA* 247: 623–628, 1982. Clinical responses have been reported in avascular necrosis of hips in adults and Legg-Perthes's disease in children. Bassett et al., *Clin. Orthop.* 246: 172–176, 1989; Aaron et al., *Clin. Orthop.* 249: 209–218, 1989; Harrison et al., *J. Pediatr. Orthop.* 4: 579–584, 1984. It has also been shown that PEMFs (Mooney, *Spine,* 15: 708–712, 1990) and capacitive coupling (Goodwin, Brighton et al., *Spine,* 24:

1349–1356, 1999) can significantly increase the success rate of lumbar fusions. There are also reports of augmentation of peripheral nerve regeneration and function and promotion of angiogenesis. Bassett, *Bioessays* 6: 36–42, 1987. Patients with persistent rotator cuff tendonitis refractory to steroid injection and other conventional measures, showed significant benefit compared with placebo treated patients. Binder et al., *Lancet* 695–698, 1984. Finally, Brighton et al. have shown in rats the ability of an appropriate capacitive coupling electric field to both prevent and reverse vertebral osteoporosis in the lumbar spine (Brighton et al., *J. Orthop. Res.* 6: 676–684, 1988; Brighton et al., *J. Bone Joint Surg.*, 71: 228–236, 1989).

More recently, research in this area has focused on the effects stimulation has on tissues and cells. For example, it has been conjectured that direct currents do not penetrate cellular membranes and that control is achieved via extracellular matrix differentiation (Grodzinsky, *Crit. Rev. Biomed. Eng.* 9:133, 1983). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae (Aaron et al., *J. Bone Miner. Res.* 4: 227–233, 1989). More recently, Lorich, Brighton et al. reported (*Clin. Orthop. Related Res.* 350: 246–256, 1998) that signal transduction of a capacitively coupled electric signal is via voltage gated calcium channels, leading to an increase in cytosolic calcium with a subsequent increase in activated (cytoskeletal) calmodulin.

Much research has been directed at studying tissue culture in order to understand the mechanisms of response. In one study, it was found that electric fields increased [$^3$H]-thymidine incorporation into the DNA of chondrocytes, supporting the notion that $Na^+$ and $Ca^{2+}$ fluxes generated by electrical stimulation trigger DNA synthesis (Rodan et al., *Science* 199: 690–692, 1978). Studies have found changes in the second messenger, cAMP, and cytoskeletal rearrangements due to electrical perturbations (Ryaby et al., *Trans. BRAGS* 6: 1986; Jones et al., *Trans. BRAGS* 6: 51, 1986; Brighton and Townsend, *J. Orthop. Res.* 6: 552–558, 1988). Other studies have found effects on glycosaminoglycan, sulfation, hyaluronic acid, lysozyme activity and polypeptide sequences (Norton et al., *J. Orthop. Res.* 6: 685–689, 1988; Goodman et al., *Proc. Natn. Acad. Sci. USA* 85: 3928–3932 1988).

It was reported in 1996 by the present inventor that a cyclic biaxial 0.17% mechanical strain produces a significant increase in TGF-$\beta_1$ mRNA in cultured MC3T3-E1 bone cells (Brighton et al., *Biochem. Biophys. Res. Commun.* 229: 449–453, 1996). Several significant studies followed in 1997. In one study it was reported that the same cyclic biaxial 0.17% mechanical strain produced a significant increase in PDGF-A mRNA in similar bone cells (Brighton et al., Biochem. *Biophys. Res. Commun.* 43: 339–346, 1997). It was also reported that a 60 kHz capacitively coupled electric field of 20 mV/cm produced a significant increase in TGF-$\beta_1$ in similar bone cells (Brighton et al., *Biochem. Biophys. Res. Commun.* 237: 225–229, 1997). However, the effect such a field would have on other genes has not been reported in the literature.

In the above-referenced parent patent application, entitled "Regulation of Genes Via Application of Specific and Selective Electrical and Electromagnetic Signals," methods were disclosed for determining the specific and selective electrical and electromagnetic signals for use in creating specific and selective fields for regulating target genes of diseased or injured tissues. The present invention builds upon the technique described therein by describing the method of determining the voltage and current output required and the corresponding apparatus for delivering specific and selective electrical and electromagnetic signals to the human knee joints in patients afflicted with osteoarthritis and other cartilage defects, diseases and injuries.

SUMMARY OF THE INVENTION

The present invention relates to treating osteoarthritis and other cartilage diseases, defects, and injuries in human knee joints via the application of specific and selective fields generated by specific and selective electric and/or electromagnetic signals. The invention includes a method of determining the voltage and current of the signal to apply to electrodes or coils applied to the knee for treatment.

More particularly, the invention relates to a method of treating diseased tissue in a human through the application of a specific and selective electric or electromagnetic field to diseased tissue in a human, including osteoarthritis and other cartilage diseases, defects and injuries in the knee. The method includes the steps of determining the voltage and current output that provides the treatment of diseased tissue in an animal model corresponding to the diseased tissue of the human, determining the anatomic dimensions and total tissue volume of the diseased tissue in the animal model, determining the anatomic dimensions of total tissue volume of the diseased tissue of the human, scaling of the voltage and current output used in the animal model based on the comparative anatomical dimensions and the total tissue volume of the diseased tissue of the human to the total tissue volume of the diseased tissue in the animal model, and applying the scaled voltage and current to the diseased tissue of the human.

In order to determine the anatomic and tissue volume factors of the human knee, an analytical model of the human knee was developed that accounts for the contributions to total tissue volume by the different components of the knee joint. The conductivities of the tissues between electrodes applied to the knee, the electric field amplitude for bone, cartilage, marrow, muscle and fat in the knee, the current density amplitude for bone, cartilage, marrow, muscle and fat in the knee, the electric field amplitude for different thicknesses of articular cartilage in the knee, the electric field amplitude for knees of different sizes, the electric field amplitude without subcutaneous fat in the knee, the current density amplitude with and without subcutaneous fat in the knee, the electric field amplitude and current density for at least two longitudinal positions of the electrodes relative to the knee, and variations of at least two effective driving signals applied to the body from an external signal generator are determined from derived electric field and/or current density histograms for a determination of the current and voltage signals to apply to the knee to create the desired therapeutic field.

It is understood that a single value of applied voltage, at a particular frequency, across an anatomical structure such as a knee results in a range of values of electric field and current density in each tissue compartment. This results from the spatial complexity of anatomical compartments in living structures and their different electrical properties. Accordingly, the histograms derived by this analysis presents the percent of tissue volume for which the electric field or current density has a specific value as a function of the range of electric field and current density values. For example, the application of a sine value voltage of 0.25 V amplitude at 60 kHz results in a range of peak values in the cartilage/synovium, of the electric field amplitude of approximately 8 mV/cm to 200 mV/cm in a knee the size of a rabbit knee while in a human knee a sine wave voltage amplitude of 5 V @ 60 kHz would be required to achieve the approximate overlapping range of peak values. The range of values of the electric field amplitude in the treated tissue is an important "dose" parameter in this invention.

The range of values obtained from the analytical model must encompass the values obtained from detailed studies of cellular responses to the stimulating electrical fields. One therefore measures the electrical field dose-response of cells taken from the target tissue to determine the field amplitudes that are most effective. Then, from the histograms shown, one determines the external voltage and currents to apply, first to animal models and then to humans, in order to encompass these effective electrical parameters at the tissue targeted for healing. In the example set forth here, a frequency of 60 kHz for the applied signal is used to obtain specific numerical values. Accordingly, the impedance values of all tissue compartments were taken at the frequency of 60 kHz. One knowledgeable in the field could perform the same analysis at other frequencies, adjust the tissue impedances to their values at the new frequency and obtain different values for the ranges of the electrical field and current density at any chosen frequency or set of frequencies.

The invention also includes a method and a device for treating diseased tissue (such as osteoarthritis), defective or injured tissue in a human knee joint through the application of a specific and selective electric or electromagnetic field to the afflicted tissue in the human knee joint. Such a device in accordance with a capacitive coupling embodiment of the invention includes at least two electrodes adapted for application in the proximity of a patient's knee joint and a signal generator that generates electric signals for application to the electrodes so as to produce an electric field of amplitude approximately 8 mV/cm to 360 mV/cm and a current density from approximately 8 $\mu A/cm^2$ to 300 $\mu A/cm^2$ within the synovium and articular cartilage of the patient's knee joint. An inductive coupling embodiment of the invention includes a coil adapted and configured to receive the electric signals to produce these electric fields. Preferably, the signal generator provides one of a plurality of output electric signals with a voltage selected by a user in accordance with a size of the human knee joint. Larger knee joints receive signals with larger voltages.

These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which.

DETAILED DESCRIPTION OF PREFERRED EMBODIMENTS OF THE INVENTION

The invention will be described in detail below with reference to FIGS. 1–16. Those skilled in the art will appreciate that the description given herein with respect to those figures is for exemplary purposes only and is not intended in any way to limit the scope of the invention. All questions regarding the scope of the invention may be resolved by referring to the appended claims.

Definitions

As used herein, the phrase "signal" is used to refer to a variety of signals including mechanical signals, ultrasound signals, electromagnetic signals and electric signals output by a device.

As used herein, the term "field" refers to an electrical field within targeted tissue, whether it is a combined field or a pulsed electromagnetic field or generated by direct current, capacitive coupling or inductive coupling.

Description of Illustrated Embodiments

Previous studies by the present inventors have shown that a capacitively coupled field significantly increased the proliferation of bone cells grown in culture (Brighton, Pollack, et al., *J. Orthop. Res.* 3: 331–340, 1985) and significantly increased the rate of healing in a rat fractured fibula model (Brighton, Pollack, et al., *Clin. Orthop. Related Res.* 285: 255–262, 1992). Also, the field distributions in the vertebral bodies of rats during capacitively coupled electrical stimulation have been determined (Carter, Vresilovic, Pollack, and Brighton, *IEEE Trans. Biomed. Eng.* 36(-3): 333–334, 1989). In order to determine the required output voltage and current required to produce an equivalent electric field and current density in a human knee as found in bone cell and rabbit fibula studies, the analytical model depicted in FIGS. 2 and 3 was developed in accordance with the invention for representing the typical human knee joint illustrated in FIG. 1.

Figure 1:
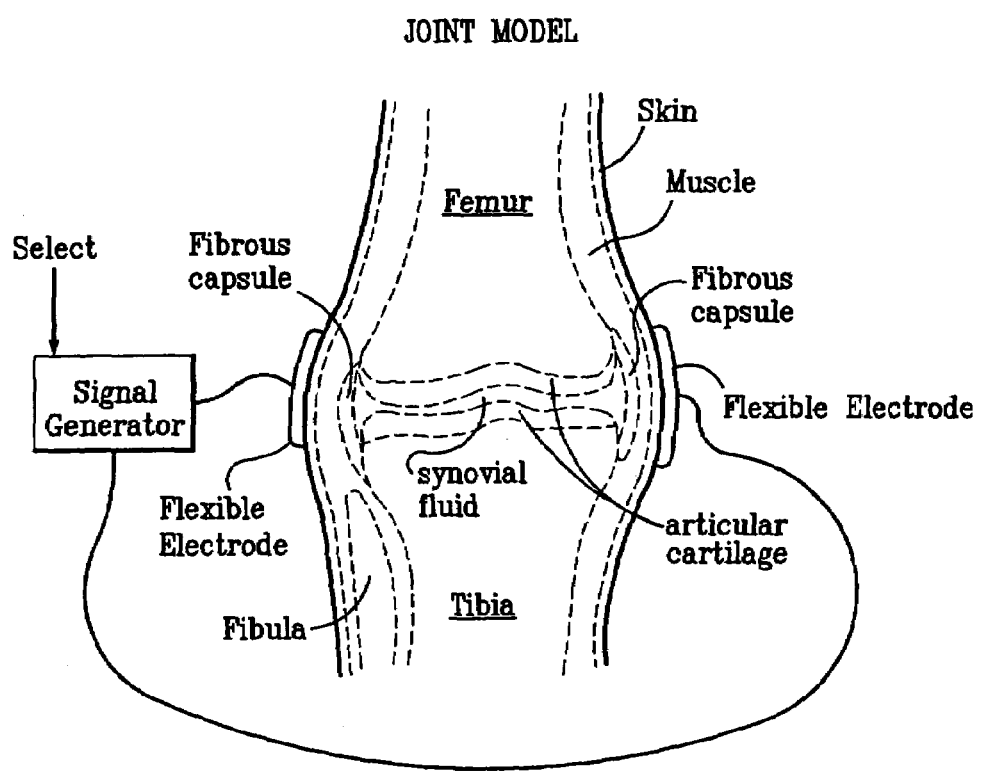
FIG. 1 illustrates a human knee joint with applied electrodes used for the treatment of osteoarthritis, cartilage defects, or as in accordance with the invention.

As shown in FIG. 1, the typical human knee joint includes a compartment filled with synovial fluid that is bounded by the articular cartilage on the ends of the femur and tibia, respectively, and fibrous capsules. In accordance with the invention, osteoarthritis in the knee joint is treated by the application of specific and selective electric fields via flexible electrodes attached relative to the knee joint substantially as shown in FIG. 1. A signal generator provides the appropriate signals to the electrodes for generating the specific and selective electric fields. The specific and selective electric field needed to treat osteoarthritis in the knee joint is calculated in accordance with the invention using the analytical model of the knee joint depicted in FIGS. 2 and 3.

Figure 2:
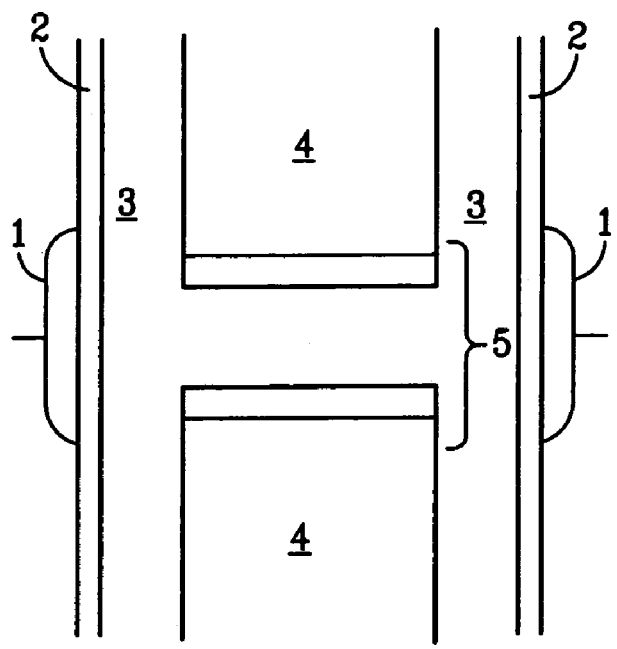
FIG. 2 illustrates a front view of an analytical model of the human knee joint of FIG. 1 for use in calculating voltage and current requirements for the treatment of osteoarthritis in accordance with the invention.
Figure 3:
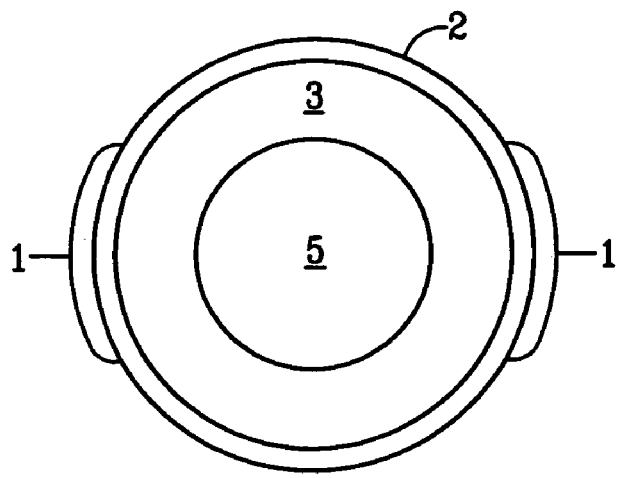
FIG. 3 illustrates a cross-sectional view of an analytical model of the human knee joint of FIG. 1 for use in calculating voltage and current requirements for the treatment of osteoarthritis in accordance with the invention.

In the analytical model of FIGS. 2 and 3, the following elements are identified as indicated: electrodes 1, skin 2, muscle 3, bone 4, and cartilage and synovial fluid compartment 5. In arriving at the analytical model, the following assumptions were made regarding the sizes of the elements: the femoral width=76.5 mm; the tibial width=101.5 mm; and the interelectrode distance=108 mm. The specific account of the electrical properties of ligaments was not included—rather, space other than cartilage and bone was considered to have the same electrical properties as muscle and marrow. Also, the conductivities of the tissues included in the study were measured as follows:

| Material | Complex Conductivity (S/m) at 60 kHz |
| --- | --- |
| Muscle | |
| Parallel to fibers | $7.0 \times 10^{-1}$ |
| Perpendicular to fibers | $2.0 \times 10^{-1}$ |
| Marrow | $2.0 \times 10^{-1}$ |
| Bone Cortex | $1.0 \times 10^{-2}$ |
| Cartilage | $8.9 \times 10^{-2}$ |
| Subcutaneous Fat | $2.0 \times 10^{-1}$ |
| | Admittance/Area (S/cm$^2$) at 60 kHz |
| Electrode-Dermal Interface | $3.0 \times 10^{-3}$ |

As will be explained below, the cartilage and synovial fluid compartment 5 was computed for three sizes: 0.3 cm, 2.3 cm, and 4.3 cm, and the applied electrode potential (potential between the two electrodes) was taken as 1.0 V.

The approximate results for the analytic model of the human knee for an applied voltage of 1.0 V peak-to-peak at 60 kHz are given below for various parameters as a function of the electric field and the current density.

Figure 4:
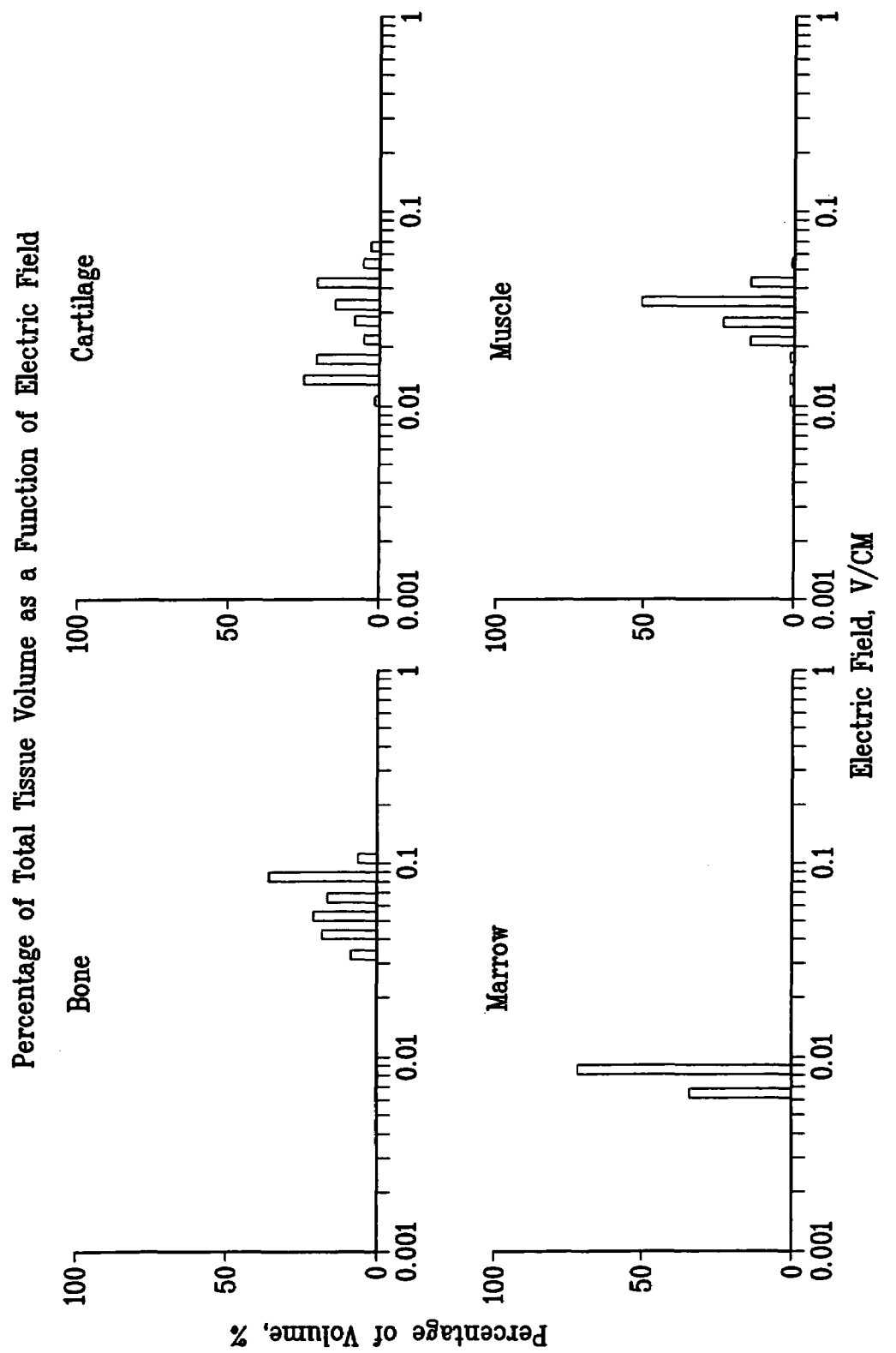
FIG. 4 illustrates electric field histograms plotting the percentage of the total tissue volume as a function of the electric field amplitude for each of the tissues.
Figure 5:
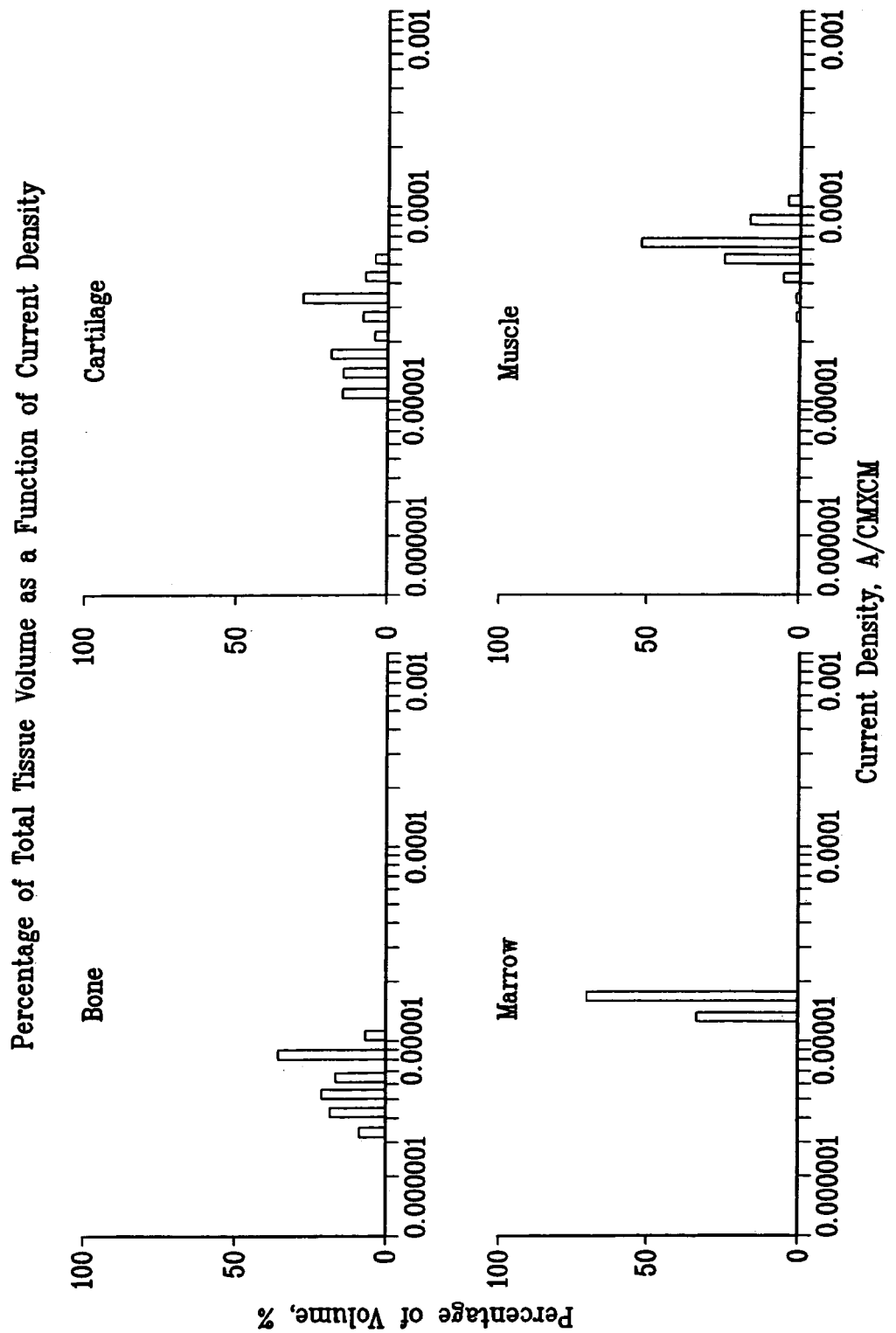
FIG. 5 illustrates current density histograms plotting the percentage of the total tissue volume as a function of the current density amplitude for each of the tissues.

As shown in FIG. 4, the electric field in the cartilage/synovial compartment 5 is not uniform in value over the entire volume of the compartment. This is also true for all compartments and reflects the complex geometry even for the analytical model. Also, as shown in FIG. 5, the current density in the cartilage/synovial fluid compartment 5 is not uniform over the volume of the compartment. This is also true for all other compartments and reflects the complex geometry even in the analytical model.

Figure 6:
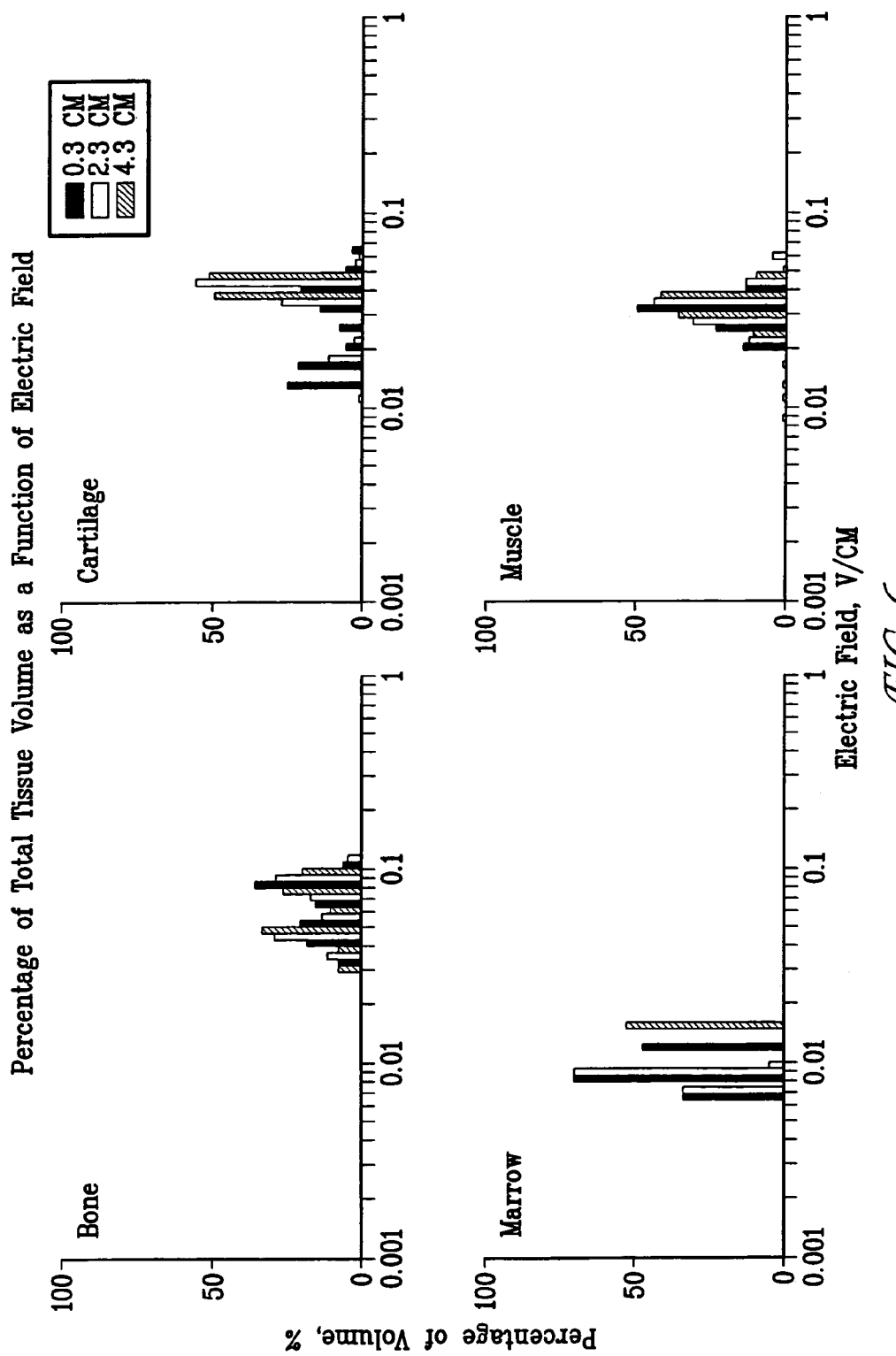
FIG. 6 illustrates the electric field histograms plotting the percentage of the total tissue volume as a function of the electric field amplitude for three values of gap width of the cartilage/synovial fluid compartment.

As shown in FIG. 6, as the cartilage/synovial fluid compartment 5 increased in thickness, the electric field in the cartilage/synovial fluid compartment 5 increased and became more uniform.

Figure 7:
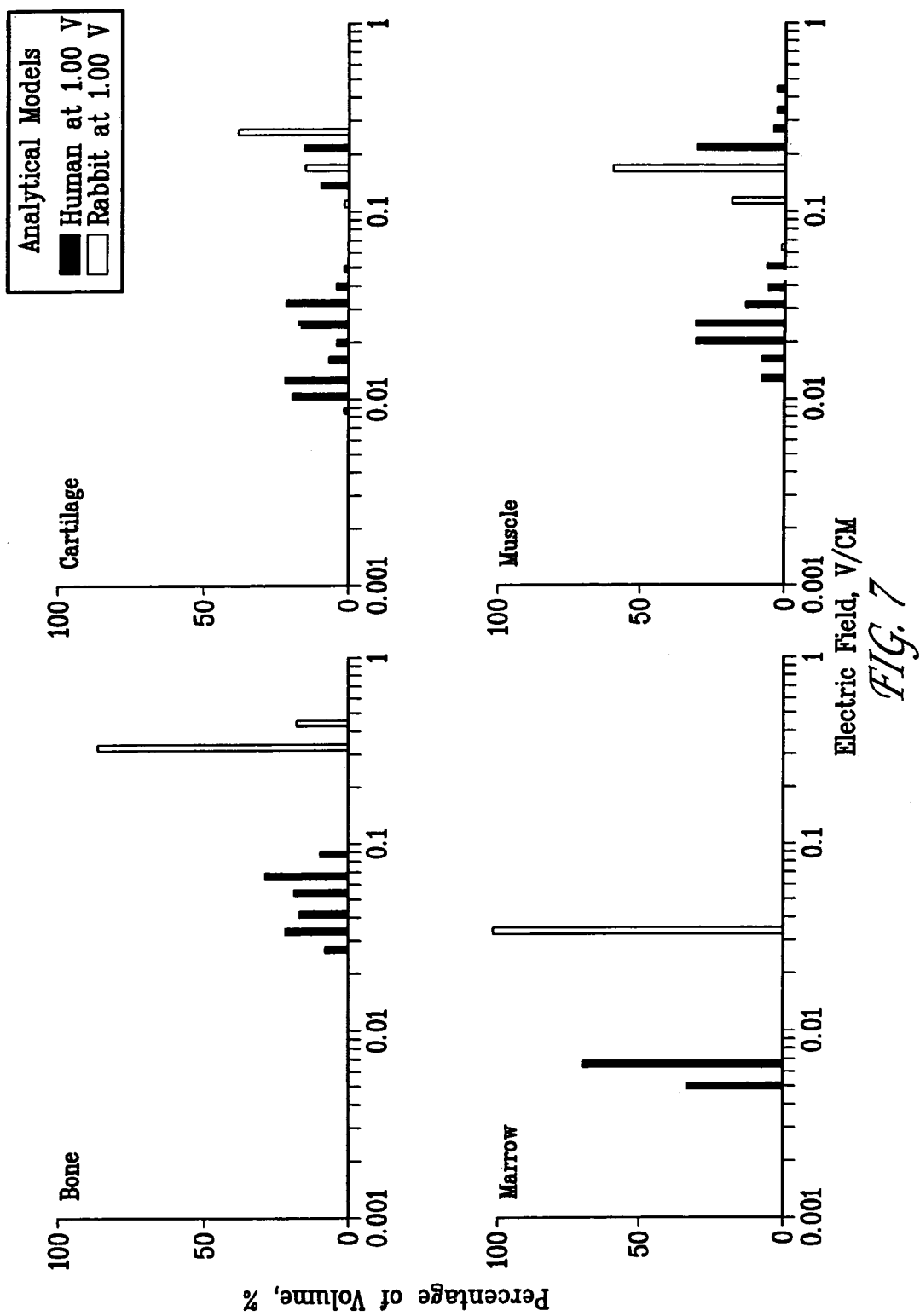
FIG. 7 illustrates electric field histograms showing that as the knee size increased from the size of a rabbit knee to the size of a human knee, the electric field in the cartilage/synovial fluid compartment decreased.
Figure 8:
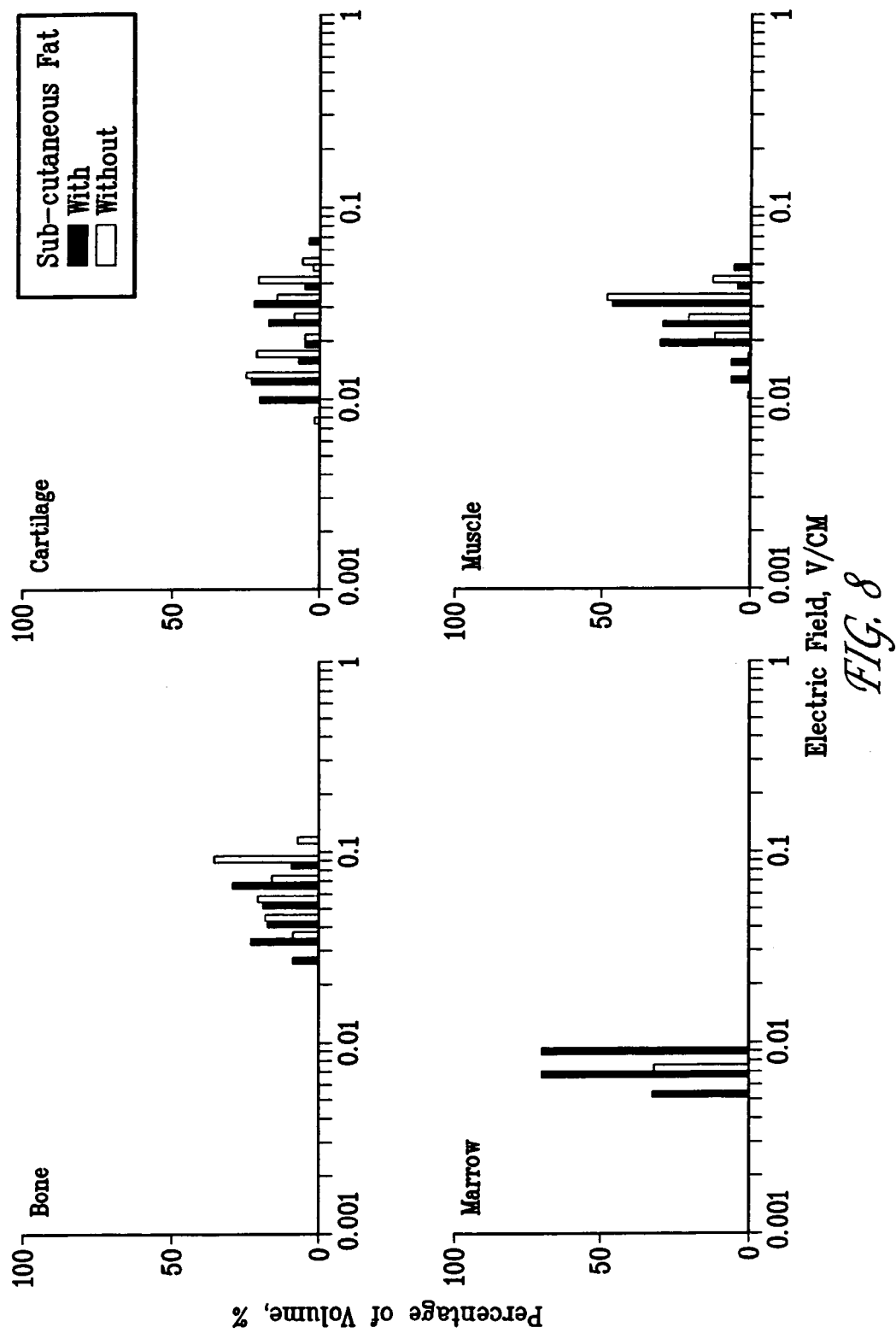
FIG. 8 illustrates electric field histograms for the analytic model of the human knee with and without subcutaneous fat.
Figure 9:
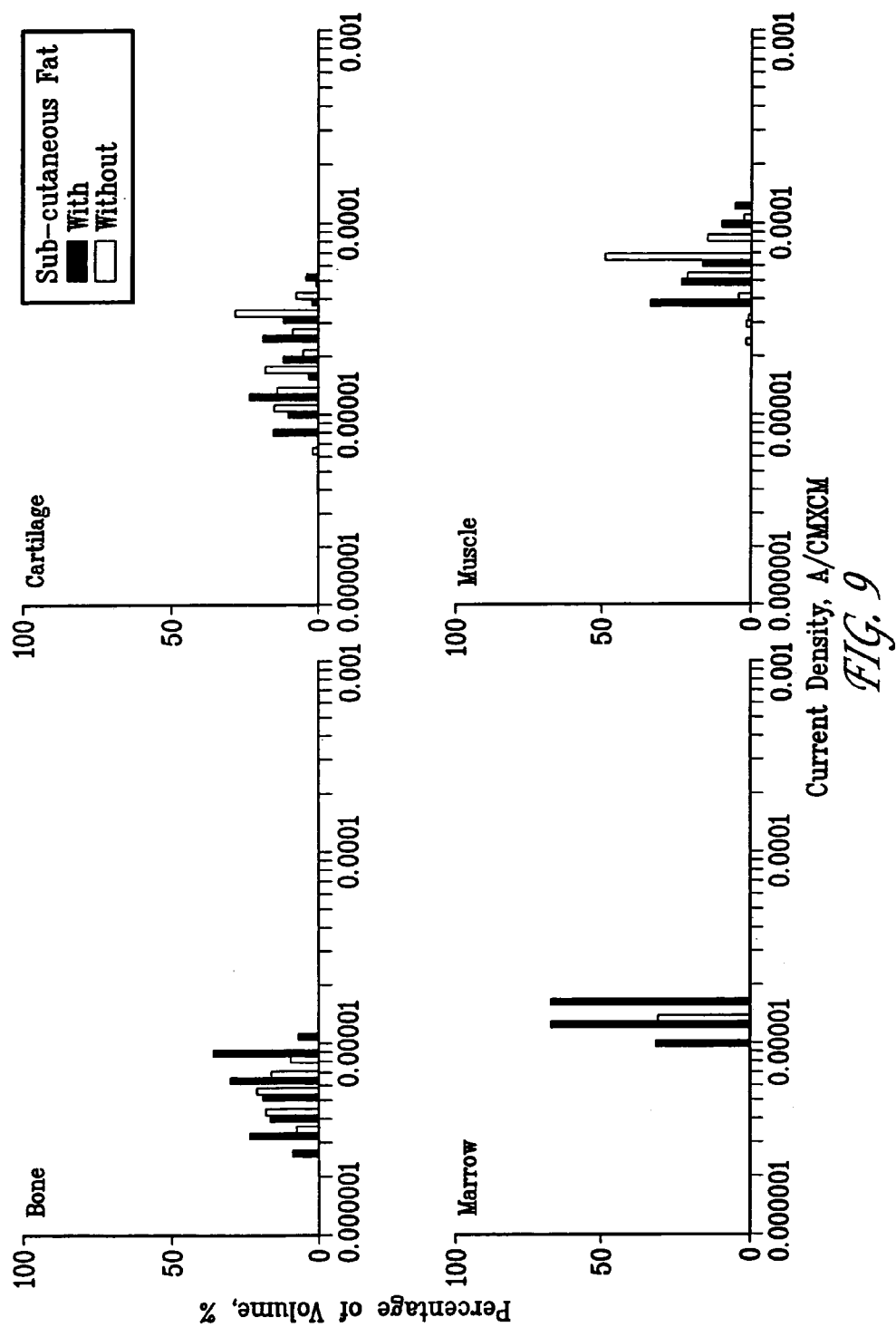
FIG. 9 illustrates current density histograms for the analytic model of the human knee with and without subcutaneous fat.

As shown in FIG. 7, as the knee size increased from the size of a rabbit knee to the size of a human knee, the electric field in the cartilage/synovial fluid compartment 5 decreased. In general, increasing or decreasing the knee diameter was found to change the entire field distribution by the reciprocal of the distance between the two electrodes. In other words, the larger the knee diameter, the smaller the electric field for a fixed applied voltage.

The amount of subcutaneous fat has also been found to have little effect on field and current density. Subcutaneous fat has a lower conductivity than muscle and, therefore, the electric field (FIG. 8) and current density (FIG. 9) are slightly decreased, but this is not substantive in most cases of the knee.

Figure 10:
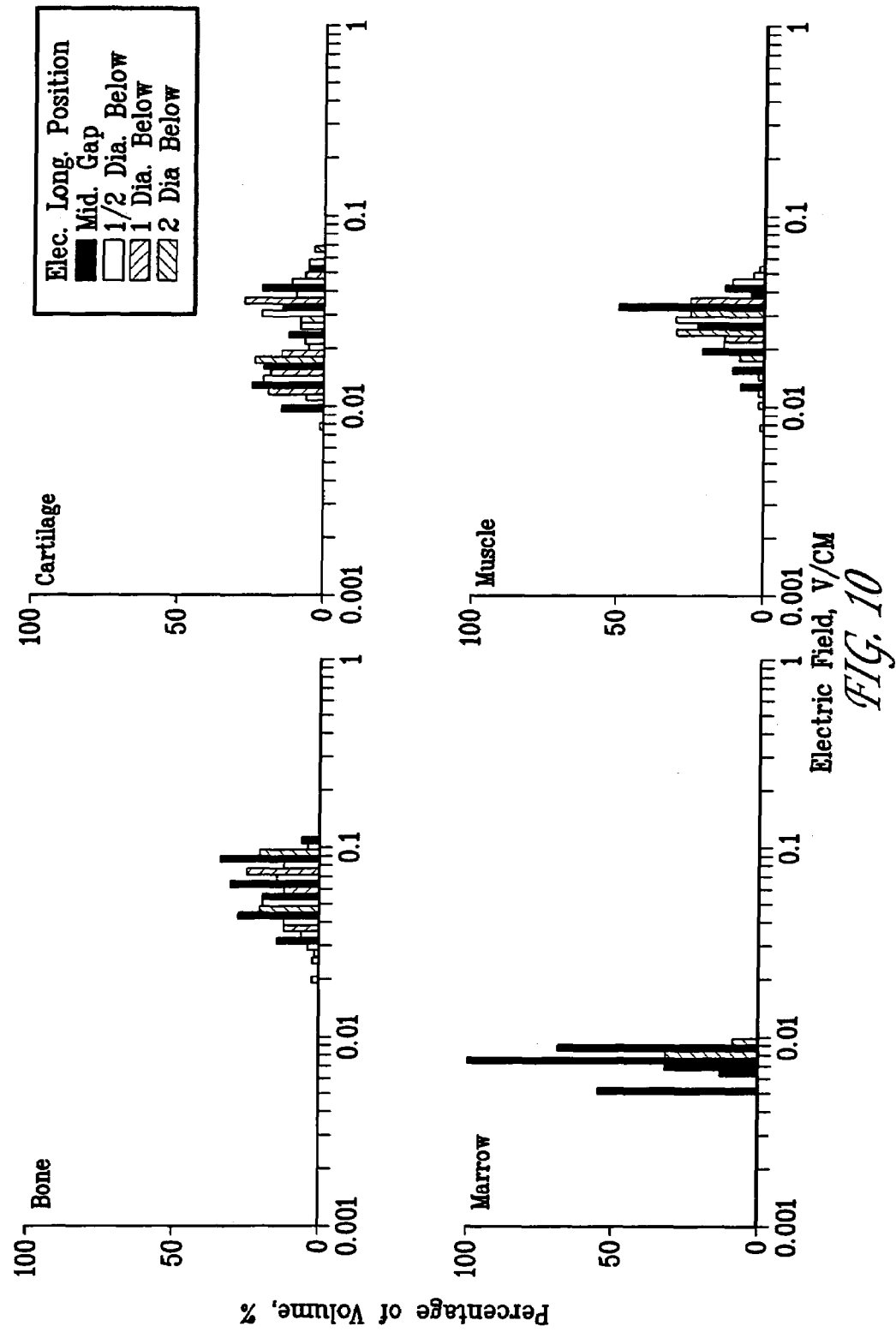
FIG. 10 illustrates electric field histograms for four longitudinal positions of the electrodes relative to the cartilage zone in the analytic model of the human knee.
Figure 11:
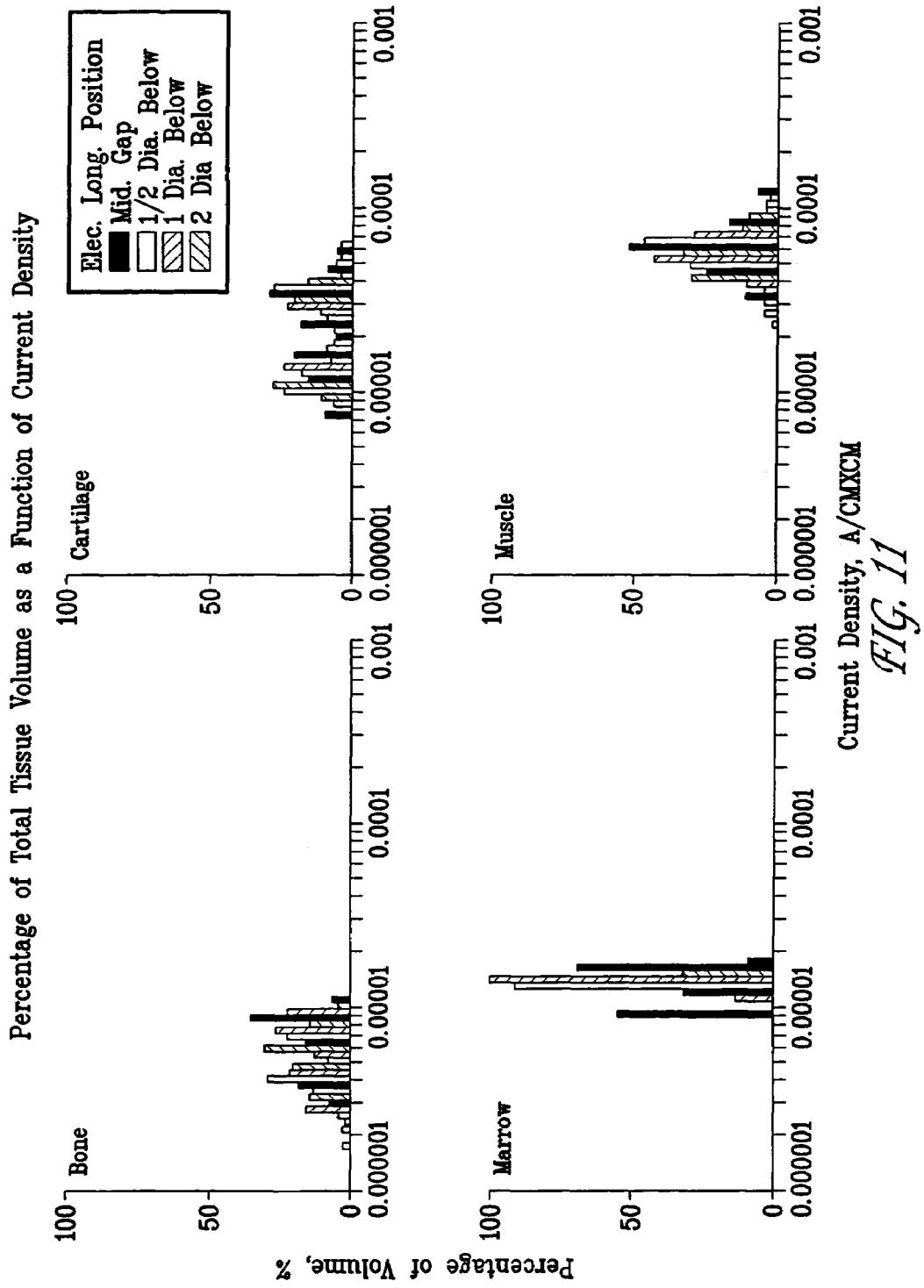
FIG. 11 illustrates current density histograms for four longitudinal positions of the electrodes relative to the cartilage zone in the analytic model of the human knee.

Finally, it has been discovered that the effect of improper alignment of the electrodes 1 placed on the knee relative to the cartilage/synovial compartment 5 is not critical. Four cases were considered: 1) mid-gap (middle of the cartilage/synovial compartment 5); 2) half diameter below the gap; 3) diameter below the gap; and 4) 2 diameters below the gap. The results for the electric field are shown in FIG. 10 and for the current density are shown in FIG. 11. Thus, alignment of the electrodes is not a critical factor in this model.

Previous work by the present inventors on stimulation of fracture healing with capacitive coupling led to the following understanding of field and current levels as a progression was made sequentially from bone cell studies to animal studies to human studies:

| | |
| --- | --- |
| Cell (in vitro) Results: | Maximum effect at 20 mV/cm electric field Current density of 200 µA/cm$^2$. |
| Animal (rabbit) Results: Successful healing of Fracture Callus | Voltage output of 0.25 $V_{p-p}$ for the device with electrodes on the rabbit knee. Approximate range of peak of the electric field of 8–200 mV/cm in the fracture callus. Approximate range of peak electrical current density 8–195 µA/cm$^2$ in the fracture callus. |
| Human (nonunion) Results: Successful healing Nonunion fracture | Voltage output of 5 $V_{p-p}$ for the device with the electrodes on the skin. Approximate range of peak electric field of 8–360 mV/cm. Electric current density of 8–300 µA/cm$^2$ |

Figure 12:
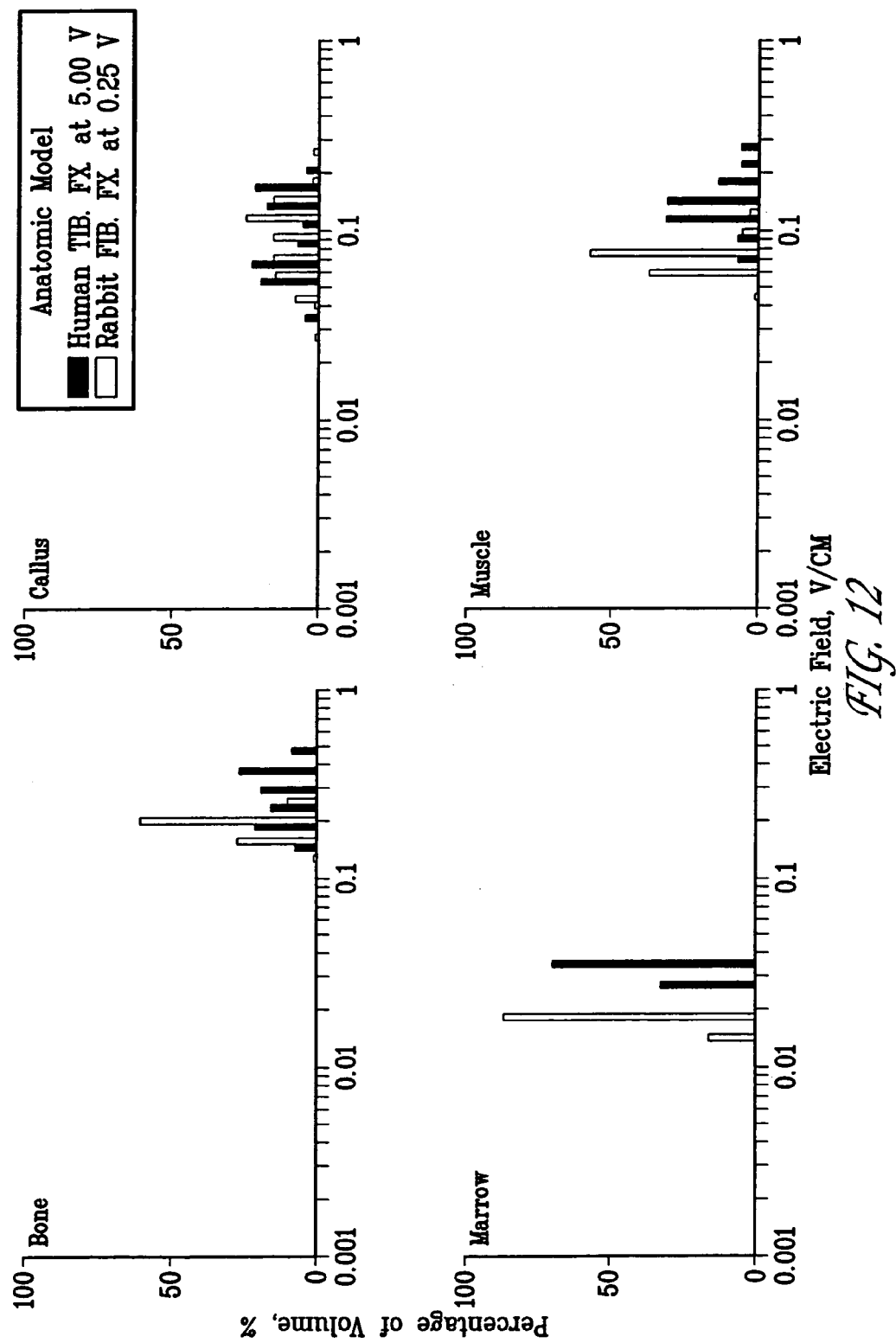
FIG. 12 illustrates electric field histograms for anatomic models of the rabbit fibular osteotomy and human tibial non-union for effective driving signals.
Figure 13:
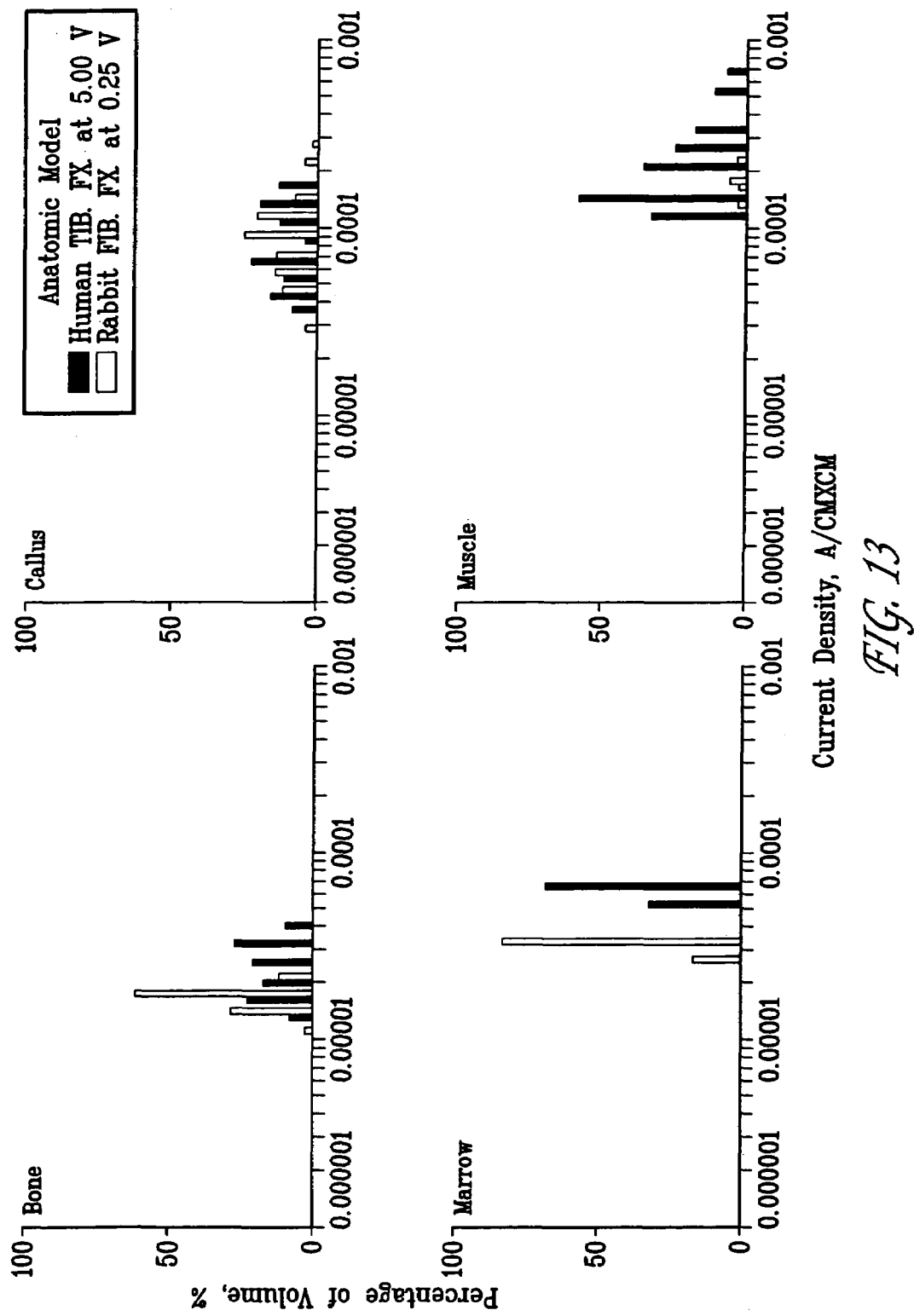
FIG. 13 illustrates current density histograms for anatomic models of the rabbit fibular osteotomy and human tibial non-union for effective driving signals.

This is shown in FIGS. 12 and 13 in which the anatomical models of both the rabbit fibula fracture model and the human nonunion model are compared. It is seen that the same successful electrical stimulation conditions are achieved at the tissue level by scaling the device voltage applied externally for treatment in accordance with the relative tissue volumes between the animal model and the human model.

As a result of these prior comparisons, the present inventors have determined the following therapeutic effective ranges of field (E) and current density in the callus (see FIG. 12: callus) and for in vitro studies of the bone cells (Brighton, Pollack, et al., *Clin. Orthop. Related Res.*, 285: 255–262, 1992) are desirable:

| (J) | Animal/Human Callus | Bone Cells |
|---|---|---|
| E | 8 mV/cm to 180 mV/cm | 20 mV/cm |
| J | 8 µA/cm² to 180 µA/cm² | 200 µA/cm |

These animal/human ranges of electrical field amplitude and current density take an important factor into account. It is that their extreme limits must encompass the results obtained from bone cell studies where geometric factors permitted more exact field determinations. In this way regions of the human/animal tissue cycle through the therapeutic effective range of the electric field and current density as the sinusoidal applied voltage cycles through the sine wave.

Since in vitro cartilage cell results also occurred at an effective field of 20 mV/cm, and since the measured circumference of the human knee joint is approximately the same as the measured diameter of the mid-calf region of the leg in a given patient, then the same scale factor of 5, used in the human tibia fracture model (FIG. 12), applies to the human knee joint analytical model of FIG. 2 where the callus is replaced by the synovial membrane and articular cartilage.

Thus, if the circumference of a given human knee=15.7 inches, then the diameter=5 inches. This was found to be the most common mean knee circumference measured in patients with osteoarthritis. An output voltage of 5 $V_{p-p}$ should produce the above E field and current density in the average size knee joint cartilage/synovial compartment. A smaller knee joint diameter, say 4.6 inches as an example, would require less voltage output (4.6 $V_{p-p}$), and a very large knee joint diameter, say 7.6 inches, would require more voltage output (7.6 $V_{p-p}$). Thus, a voltage output of 4.6 $V_{p-p}$ to 7.6 $V_{p-p}$ would cover the full range of knee sizes measured to date to produce the desired therapeutic E field and current density in the cartilage/synovial fluid compartment of the knees as described above. Variations of ±10% in the applied voltage are tolerated because of the distribution of values E and J resulting from anatomical complexity.

Thus, in accordance with the invention, the approximate size (and hence approximate diameter) of the patient's knee is determined, and a signal is generated and applied to the electrodes that will generate the desired electric field in the range of 8 mV/cm to 360 mV/cm and a current density range of 8 µA/cm² to 300 µA/cm² for treatment of osteoarthritis in the knee, for example. Preferably, the signal generator includes a select control (FIG. 1) that allows the operator to select the proper output based on the size of the patient's knee.

Figure 14:
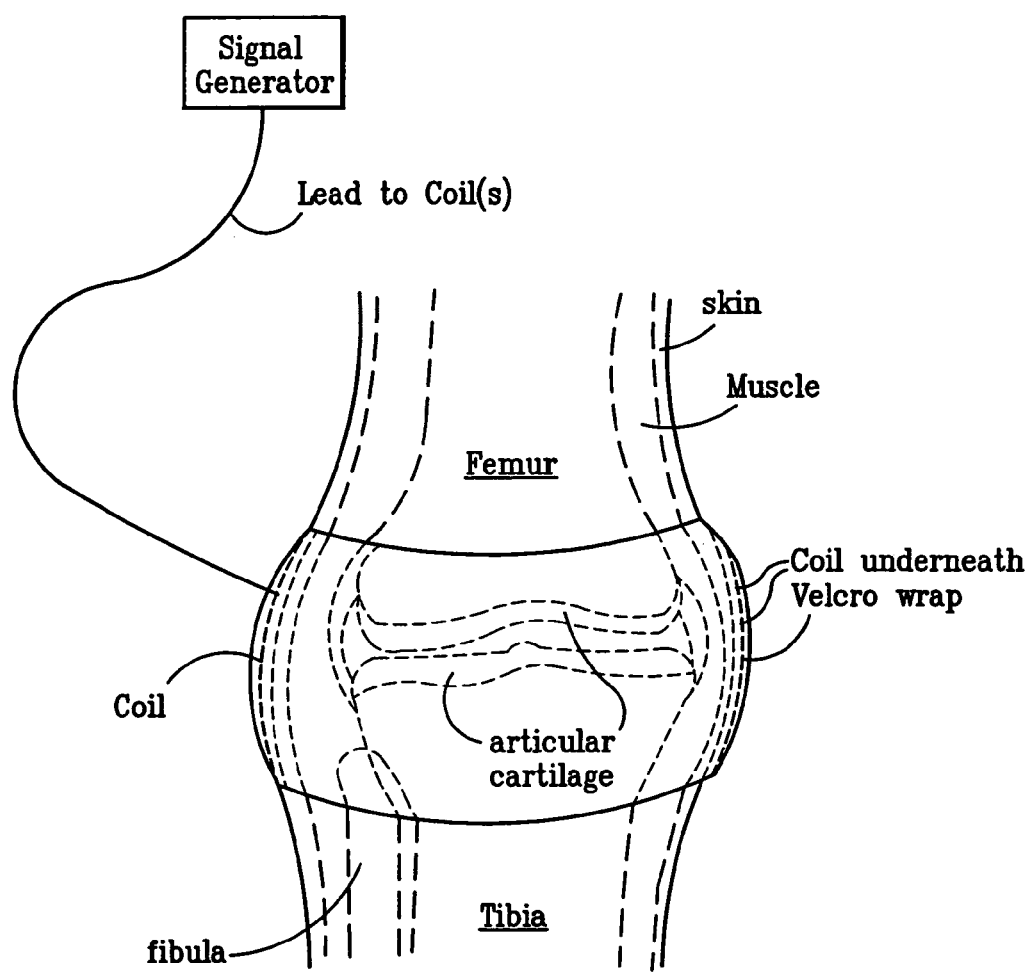
FIG. 14 illustrates a human knee joint with applied coils used for the treatment of osteoarthritis, cartilage defects due to trauma or sports injury, or used as an adjunct with other therapies (cell transplantation, tissue-engineered scaffolds, growth factors, etc.) in treating cartilage defects using inductive coupling.

Also in accordance with the invention, the appropriate electric field can be delivered to diseased or traumatized articular cartilage using an inductive coupling device of the type shown in FIG. 14. To calculate the electric field generated by the coil in FIG. 14, we imagine an elastic bandage containing a coil of N turns that is slipped over the knee and centered thereon. A battery-powered supply of current is attached to the coil leads such that a time varying current flows through the coil. This current produces a magnetic flux which in turn produces a time-varying electric field. It is understood that the current amplitude, frequency, duty cycle and wave form(s) can be controlled from the power supply so as to produce a therapeutic value for the E field. We now calculate the combinations that will accomplish this.

Figure 15:
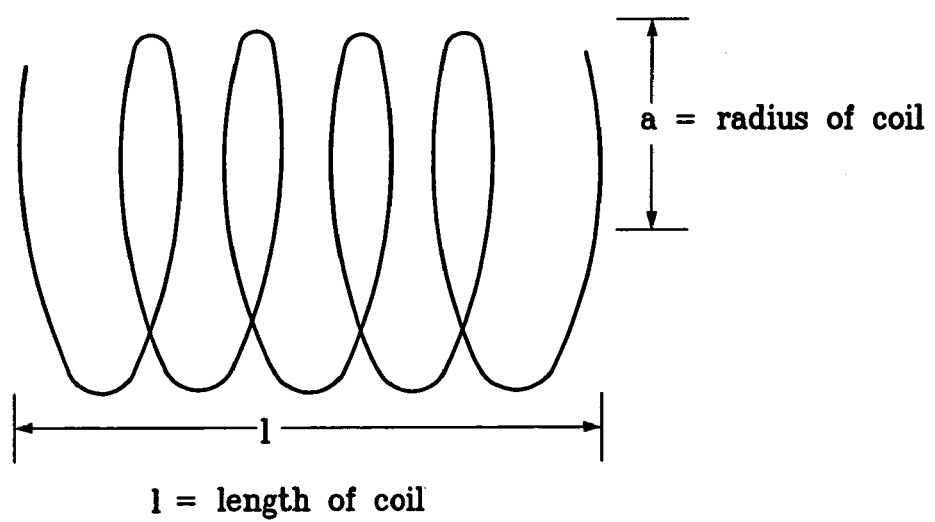
FIG. 15 illustrates a coil of N total turns of wire of radius a and length l used in determining the dimensions and number of turns of wire required to make a coil for producing the desired electric field in the articular cartilage when using inductive coupling.
Figure 16:
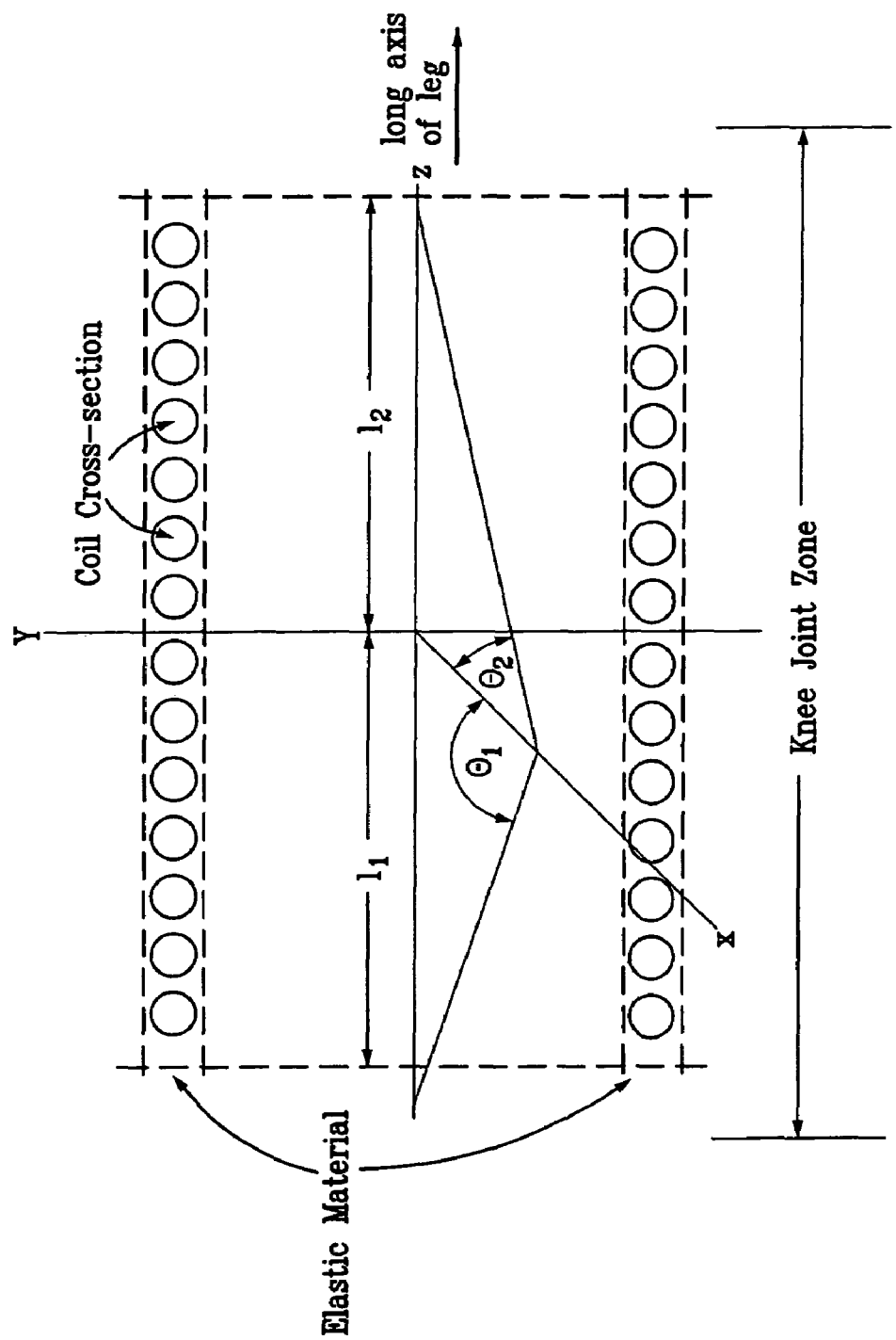
FIG. 16 illustrates the cross-section through a coil in relation to the knee joint zone along the axis at which the magnetic flux is calculated.

Schematic diagrams showing a coil of N total turns of wire and a cross-section through this coil are shown in FIGS. 15 and 16, respectively. The angles $\theta_1$ and $\theta_2$ are those between the point on the X-axis at which the magnetic flux is calculated and the ends of the coil in the +Z and −Z directions. For arbitrary sizes, the flux is given by the equation:

$$B = \frac{1}{2}\mu_0 \frac{N}{l} I(\sin\theta_2 - \sin\theta_1) \quad (1)$$

$$\text{where } \sin\theta_1 = \frac{l_1}{\sqrt{l_1^2 + a^2}}$$

$$\sin\theta_2 = \frac{l_2}{\sqrt{l_2^2 + a^2}}$$

and I is the current in the coil, l is the length of the coil and $\mu_0$ is the magnetic permeability of air (and tissue). In the central region of the coil, the field of a solenoid is quite uniform so we can select the values of $l_1$ and $l_2$ so that they are equal. Since $\sin\theta_1$ is a negative number because $l_1$ is negative along the Z axis, $\sin\theta_2 - \sin\theta_1 = 2 \sin\theta_2$ if $l_1 = l_2$.

Therefore, Equation (1) becomes:

$$B = \mu_0 \frac{N}{l} I \left( \frac{l}{(l^2 + 4a^2)^{\frac{1}{2}}} \right) \quad (2)$$

The current, I is a sinusoidal varying current and it can be written as:

$$I = I_0 e^{i\omega t} \quad (3)$$

where $I_0$ is the amplitude of the sinusoidal current, ω is 2π times the frequency (which we will set to 60 kHz, and i is the imaginary number $\sqrt{-1}$. This notation is equivalent to the following:

$$I = I_0 \sin \omega t \quad (4)$$

Therefore, Equation (2) becomes:

$$B = \mu_0 \frac{N}{l} I_0 \left( \frac{l}{(l^2 + 4a^2)^{\frac{1}{2}}} \right) \sin\omega t \quad (5)$$

From Maxwell's Equations we obtain an expression for the amplitudes of the electric field associated with the time-varying magnetic flux. It should be noted that the magnetic flux is parallel to the long axis of the leg and is therefore perpendicular to the planes of the cartilage in the knee. The electric field, however, is in the planes of the cartilage, is circular in direction, and will vary in amplitude with radius such that at the geometric center of the knee, the electric field amplitude will be zero and it will increase in amplitude in a linear dependence on radius.

The theory says that $$|E| = -\frac{dB}{dt} \cdot \frac{r}{2} \quad (6)$$

where |E| is the electric field amplitude, dB/dt is the time derivative of Equation (5), and r is the distance from the geometric center of the knee joint to an arbitrary radius, r. Placing Equation (5) into equation (6) and performing differentiation gives $$|E| = \mu_0 \frac{N}{l} I_0 \omega \cos\omega t \left( \frac{l}{(l^2 + 4a^2)^{\frac{1}{2}}} \right) \cdot \frac{r}{2} \quad (7)$$

where the cos ω indicates that the electric field is 90° out of phase with the magnetic flux.

If we insert the values of all the parameters in Equation (7), namely $$a = 6.35 \times 10^{-2} \text{ meters}$$
$$l = 6.35 \times 10^{-2} \text{ meters}$$
$$\mu_0 = 4\pi \times 10^{-7} T \text{ meters/A}$$
$$N = 3 \times 10^3 \text{ turns}$$
$$I_0 = 100 \text{ mA}$$
$$r = 6.35 \times 10^{-2} \text{ meters}$$
$$\omega = 2\pi \times 60 \times 10^3 \frac{1}{\sec}$$

we obtain $$|E|_{Max} = 315 \text{ mV/cm}$$

where $|E|_{Max}$ is the amplitude at the maximum radius of the knee, namely $6.35 \times 10^{-2}$ meters.

Therefore, for any given cycle of the magnetic field, the center of the knee has zero electric field, while at the extreme radius, the field cycles from 0 to 315 mV/cm. For 90% of the area of the cartilage synovial region to achieve an electric field strength of 20 mV/cm, the maximum field at the periphery of the knee joint must be 65 mV/cm. This means that the number of turns (N) in the transducer can be reduced from 3000 to (65/315)×3000=620.

Although implementations of the invention have been described in detail above, those skilled in the art will readily appreciate that many additional modifications are possible without materially departing from the novel teachings and advantages of the invention. Any such modifications are intended to be included within the scope of the invention as defined in the following claims.

What is claimed is:

1. A method of treating diseased tissue in a human through the application of a specific and selective electric or electromagnetic field to the diseased tissue in the human, comprising the steps of:
   a. determining the voltage and current output that provides the treatment of diseased tissue in an animal model corresponding to the diseased tissue of the human;
   b. determining the total tissue volume of the diseased tissue in the animal model;
   c. determining the total tissue volume of the diseased tissue of the human;
   d. determining conductivities of the diseased tissue of the human between at least two electrodes;
   e. scaling the voltage and current output used in the animal model based on the anatomic size and the ratio of the total tissue volume of the diseased tissue of the human to the anatomic size and the total tissue volume of the diseased tissue in the animal model; and
   f. applying the scaled voltage and current to the diseased tissue of the human.

2. The method of claim 1 wherein the scaled voltage and current applying step comprises the step of applying the scaled voltage and current to the human using two electrodes in the case of capacitive coupling.

3. The method of claim 1 wherein the scaled voltage and current applying step comprises the step of applying the scaled voltage and current to the human using a solenoid or coil in the case of inductive coupling.

4. The method of claim 1 wherein the human tissue volume determining step comprises the step of using an analytical model of the human knee.

5. The method of claim 1 wherein the human tissue volume determining step comprises the step of determining the applied electrode potential for cartilage and synovial compartments of two or more sizes using the conductivities of the tissues between at least two electrodes.

6. The method of claim 1 wherein the human tissue volume determining step comprises the step of determining the percentage of total tissue volume as a function of the electric field amplitude for bone, cartilage, marrow, muscle and fat in the knee of the patient using electric field histograms.

7. The method of claim 1 wherein the human tissue volume determining step comprises the step of determining the percentage of total tissue volume as a function of the current density amplitude for bone, cartilage, marrow, muscle and fat in the knee of the patient using current density histograms.

8. The method of claim 1 wherein the human tissue volume determining step comprises the step of determining the percentage of total tissue volume as a function of the electric field amplitude for different thicknesses of articular cartilage in the knee using electric field histograms.

9. The method of claim 1 wherein the human tissue volume determining step comprises the step of determining the percentage of total tissue volume as a function of the electric field amplitude for knees of different sizes using electric field histograms.

10. The method of claim 1 wherein the human tissue volume determining step comprises the step of determining the percentage of total tissue volume as a function of the electric field amplitude without subcutaneous fat in the knee of the patient using electric field histograms.

11. The method of claim 1 wherein the human tissue volume determining step comprises the step of determining the percentage of total tissue volume as a function of the current density amplitude with and without subcutaneous fat in the knee of the patient using current density histograms.

12. The method of claim 1 wherein the human tissue volume determining step comprises the step of determining the percentage of total tissue volume as a function of the electric field amplitude for at least two longitudinal positions of the electrodes relative to the knee of the patient using electric field histograms.

13. The method of claim 1 wherein the human tissue volume determining step comprises the step of determining the percentage of total tissue volume as a function of the current density for at least two longitudinal positions of the electrodes relative to the knee of the patient using current density histograms.

14. The method of claim 1 wherein the human tissue volume determining step comprises the step of determining the percentage of total tissue volume as a function of at least two effective driving signals applied to the body from an external signal generator using electric field histograms.

15. The method of claim 1 wherein the human tissue volume determining step comprises the step of determining the percentage of total tissue volume as a function of at least two effective driving signals applied to the body from an external signal generator using current density histograms.

16. A device for treating diseased tissue in a human knee joint through the application of a specific and selective electric or electromagnetic field to the diseased or injured tissue in the human knee joint, comprising:
   a. one of (a) at least two electrodes, in the case of capacitive coupling, adapted for application in the proximity of a patient's knee joint; and (b) a solenoid or at least one coil, in the case of inductive coupling, adapted for application in the proximity of a patient's knee joint; and
   b. a signal generator having a select control that selects, based on the size of the patient's knee joint, electric signals for application to the electrodes, the solenoid or at least one coil so as to produce an electric field range of approximately 8 mV/cm to 360 mV/cm and a current density range of approximately 8 $\mu A/cm^2$ to 300 $\mu A/cm^2$ within the synovium and articular cartilage of the patient's knee joint.

17. A device for treating osteoarthritis, cartilage defects due to trauma or sports injury, or used as an adjunct with other therapies for treating cartilage defects in a human knee joint through the application of a specific and selective electric or electromagnetic field to the afflicted tissue in the human knee joint, comprising:
   a. one of (a) at least two electrodes and (b) a solenoid or at least one coil adapted for application in the proximity of a patient's knee joint; and
   b. a signal generator having a select control that selects, based on the size of the patient's knee joint, electric signals for application to the electrodes, the solenoid or at least one coil so as to produce an electric field range of approximately 8 mV/cm to 360 mV/cm and a current density of approximately 8 $\mu A/cm^2$ to 300 $\mu A/cm^2$ within the synovium and articular cartilage of the patient's knee joint.

18. A device as in claim 17, wherein the signal generator provides one of a plurality of output electric signals with a voltage selected by a user in accordance with a size of the human knee joint.

19. A device as in claim 18, wherein one of the plurality of output electrical signals of the signal generator for a 60 kHz frequency has a voltage of approximately 4.6 $V_{p-p}\pm 10\%$ for a small size knee joint.

20. A device as in claim 18, wherein one of the plurality of output electrical signals of the signal generator for a 60 kHz has a voltage of approximately 5.0 $V_{p-p}\pm 10\%$ for an average size knee joint.

21. A device as in claim 18, wherein one of the plurality of output electrical signals of the signal generator for a 60 kHz has a voltage of approximately 5.6 $V_{p-p}\pm 10\%$ for a large size knee joint.

22. A device as in claim 18, wherein one of the plurality of output electrical signals of the signal generator for a 60 kHz has a voltage of approximately 7.6 $V_{p-p}\pm 10\%$ for an extra large size knee joint.

23. A method of treating osteoarthritis, cartilage defects due to trauma or sports injury, or used as an adjunct with other therapies for treating cartilage defects in a human knee joint through the application of a specific and selective electric or electromagnetic field to the afflicted tissue in the human knee joint, comprising the steps of:
   a. converting electric potential into an electric signal that when applied to one of (a) at least two electrodes and (b) a solenoid or at least one coil adapted for application in the proximity of a patient's knee joint produces an electric field range of not less than approximately 8 mV/cm to 360 mV/cm and a current density of range approximately 8 $\mu A/cm^2$ to 300 $\mu A/cm^2$ within the synovium and articular cartilage of the patient's knee joint; and
   b. applying the electrical signal to either (a) the at least two electrodes or (b) the solenoid or at least one coil so as to produce the electric field within the synovium and articular cartilage of the patient's knee joint.

24. A method as in claim 23, comprising the additional step of selecting one of a plurality of output electric signals with a voltage in accordance with a diameter of the human knee joint.

25. A method as in claim 24, wherein the selecting step comprises the step of selecting an electrical signal of a 60 kHz frequency having a voltage of approximately 4.6 $V_{p-p}\pm 10\%$ for a small size knee joint.

26. A method as in claim 24, wherein the selecting step comprises the step of selecting an electrical signal of a 60 kHz frequency having a voltage of approximately 5.0 $V_{p-p}\pm 10\%$ for an average size knee joint.

27. A method as in claim 24, wherein the selecting step comprises the step of selecting an electrical signal of a 60 kHz frequency having a voltage of approximately 5.6 $V_{p-p}\pm 10\%$ for a large size knee joint.

28. A method as in claim 24, wherein the selecting step comprises the step of selecting an electrical signal of a 60 kHz frequency having a voltage of approximately 7.6 $V_{p-p}\pm 10\%$ for an extra large size knee joint.

* * * * *